United States Patent [19]

Curtin

[11] Patent Number: 5,174,037

[45] Date of Patent: Dec. 29, 1992

[54] METHOD AND APPARATUS FOR MEASURING PHYSICAL ATTRIBUTES OF A HUMAN BODY

[76] Inventor: Marilyn Curtin, 2241 Woodside La., #11, Sacramento, Calif. 95825

[21] Appl. No.: 705,859

[22] Filed: May 28, 1991

Related U.S. Application Data

[63] Continuation-in-part of Ser. No. 367,080, Apr. 17, 1990, abandoned.

[51] Int. Cl.⁵ .......................... A41H 1/02; G01B 3/02
[52] U.S. Cl. .......................................... 33/512; 33/1 B
[58] Field of Search ................. 33/512, 511, 1 B, 1 F, 33/1 BB, 1 C, 23.09, 562, 563; 128/774

[56] References Cited

U.S. PATENT DOCUMENTS

| | | | |
|---|---|---|---|
| 752,617 | 2/1904 | DePue | 33/1 B |
| 1,462,850 | 7/1923 | Clark | 33/551 |
| 2,752,689 | 7/1956 | Adams et al. | 33/1 B |
| 2,780,004 | 2/1957 | Rosenbaum | 33/512 |
| 3,465,450 | 9/1969 | Hamilton | 33/511 |
| 4,135,498 | 1/1979 | McGee | 33/512 |
| 4,173,074 | 11/1979 | Newman et al. | 33/512 |
| 4,407,070 | 10/1983 | Lowe | 33/511 |
| 4,779,346 | 10/1988 | Schafer | 33/1 B |
| 4,823,476 | 4/1989 | Curtin | 33/512 |

*Primary Examiner*—William A. Cuchlinski, Jr.
*Assistant Examiner*—C. W. Fulton
*Attorney, Agent, or Firm*—Skjerven, Morrill, Macpherson, Franklin and Friel

[57] ABSTRACT

Apparatus for measuring characteristics of a human head includes transparent grid members which are placed in front and at the side of a human head or an image of a human head. The grid members have vertical centerlines which are aligned with the center of the bridge of the nose and the front of the ear, respectively, and horizontal centerlines crossing the vertical centerlines. The horizontal centerlines have a number of spaced vertical scaling lines for measurement of distances on the head from the vertical centerlines, the vertical centerlines having a number of spaced horizontal scaling lines for measurement of distances on the head from the horizontal centerlines. Each grid member has an overlay of a pattern of symmetrical squares thereon to facilitate measurement.

4 Claims, 5 Drawing Sheets

LOWER HEAD
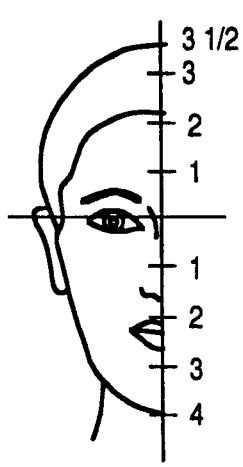
Fig. (3a)
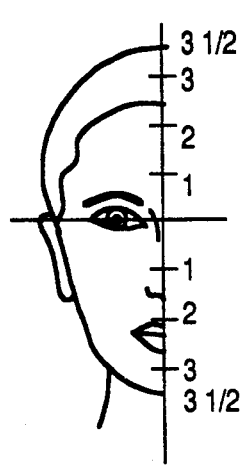
Fig. (3b)
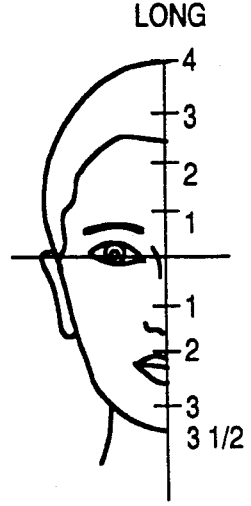
Fig. (3c)
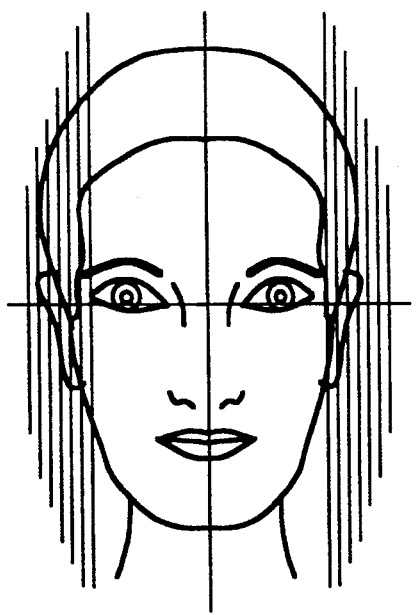
Fig. 4(a)
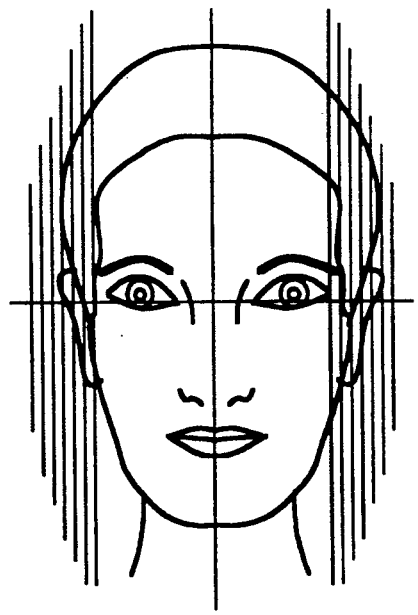
Fig. 4(b)

UPPER SECTION

SHORT

EQUAL

WIDE

BACK SECTION

SHORT

EQUAL

WIDER

ABOVE THE EYE

EVEN WITH EYE

METHOD AND APPARATUS FOR MEASURING PHYSICAL ATTRIBUTES OF A HUMAN BODY

CROSS-REFERENCE TO RELATED APPLICATION

This application is a continuation-in-part of application Ser. No. 07/367,080, filed Apr. 17, 1990, now abandoned. U.S. Pat. No. 4,823,476, issued Apr. 25, 1989 to the same inventor as named herein, has claims directed to the structure for measuring attributes of a human body according to principles disclosed in this application.

BACKGROUND OF THE INVENTION

1. Field of the Invention

This invention relates in general to methods and apparatus for measuring selected attributes of a human body, and relates more particularly to measuring such attributes in relation to the values of these attributes in a theoretically ideal human head.

2. Prior Art

Leonardo DaVinci developed a scientific scale of measurement employing a comprehensive set of proportions for drawing the human figure. He did extensive research on the human body and bone structure, and used this research in much of his art work. According to principles used by Leonardo, the height of the head becomes a "yardstick" to measure the rest of the body. In this concept of an ideal body, the entire body height is eight times the height of the head. DaVinci's principles using head height in relation to the rest of the body are:

1. Starting from the feet, the distance to the base of the calf is one head.
2. The distance from the base of the calf to the bottom of the knee is the next head.
3. To mid-thigh is three heads.
4. To the top of the thigh is four heads and the midpoint of the body.
5. The fifth part is from mid-point (top of thigh) to the waist.
6. The sixth part is from waist to the underarm.
7. The seventh part is from underarm to the chin.
8. The head itself is the eighth section.

For understanding the entire human body structure, it is important to divide the body into these small sections, seeing each individually, in order to put the body back together in a way that makes sense.

SUMMARY OF THE INVENTION

The present invention expands on DaVinci's principles to develop methods and apparatus for measuring a plurality of attributes of a human head in relation to the values of these attributes for a theoretically ideal human head.

An important aspect of the present invention involves the use of one or more transparent members having grids thereon which are positioned adjacent to a human face, or an image thereof, to enable the measurement and detection of variations in characteristics of the human head from the ideal head. These measured variations may then be used to aid in the selection of a number of factors affecting the human head.

BRIEF DESCRIPTION OF THE DRAWINGS

FIGS. 3a, 3b and 3c show the use of the invention to detect differences in the size of the upper and lower portions of the head;

FIGS. 4a and 4b show the detection of the relationship between the widths of the right and left halves of the human face;

As shown in FIG. 1, a transparent member 21 contains grid lines which are useful in analyzing the bone structure and symmetry of the human head. Member 21 contains a vertical centerline 21a which is adapted to be aligned with a vertical line extending through the center of the bridge of the human nose. Centerline 21a contains a number of different, graduated horizontal lines as shown, for measuring distances to different portions of the human head from a reference horizontal line. Member 21 also contains a reference horizontal line 21b having a number of graduated vertical markings thereon for determining distances to different facial features from the vertical centerline of the head. Member 2 also preferably has a symmetrical grid pattern thereon to facilitate measurements. Such a grid pattern may be in the form of a pattern of smaller squares 21c, such as ¼ inch in size and with light lines, and an overlying pattern of larger size such as 1 inch squares with darker or more intense lines.

Member 21 is intended as a tool to detect and analyze the bone structure of the individual with the measured characteristics being used, for example, to design a hairstyle, select appropriate eyelashes, earrings, etc. This is an extension of one of DaVinci's concepts; breaking the head into separate parts. For example, the front view of the head provided by member 21 provides information as to how high a hair style should be and where the fullness should be in the hair style. It also provides information as to where the ears are placed. A woman's earring size will depend a great deal on how long her ears are and also the contour of her face. Member 21 can also be used to design eyeglass frames, with the eyeglass frame following the structure of the face. Further, centerline 21a extending through the center of a nose provides a measure of the extent of crookedness in a nose, which can also be used as a guide in plastic surgery.

Figure 1:
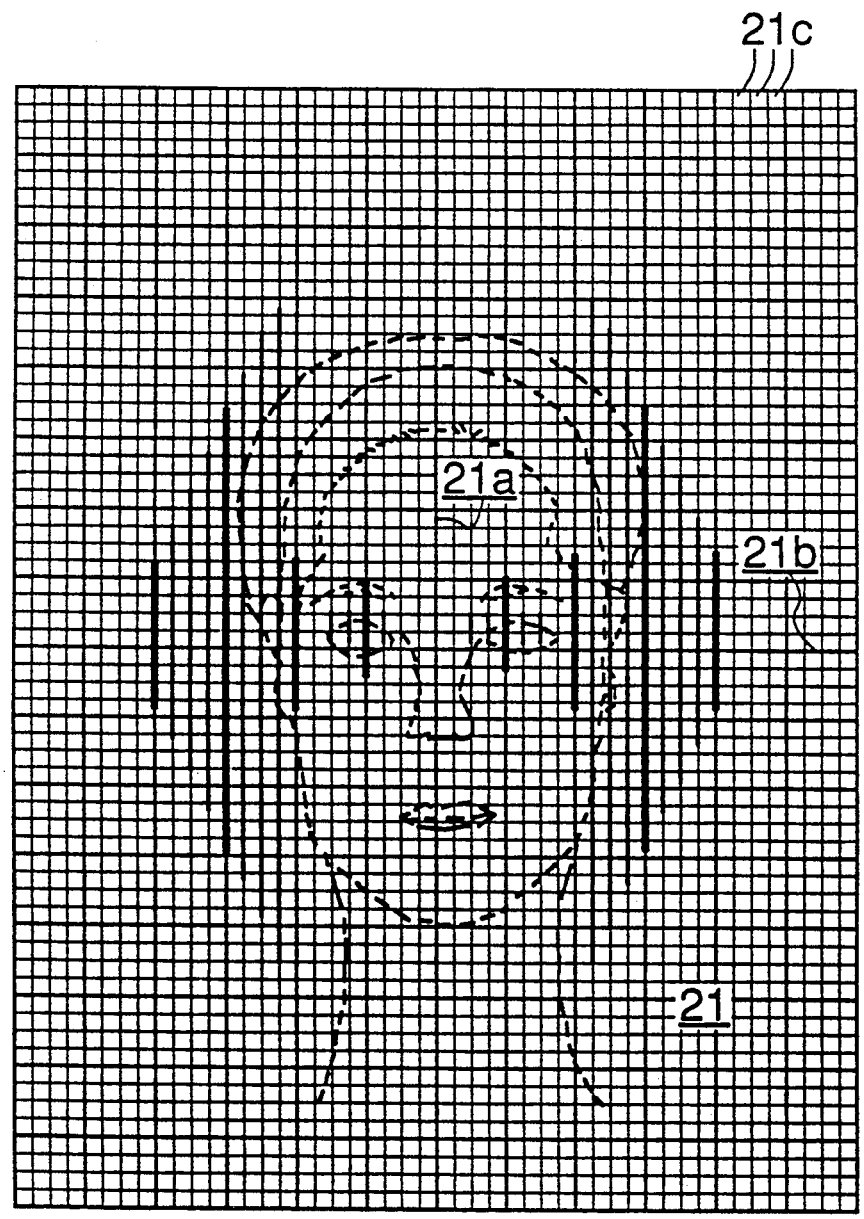
FIGS. 1 and 2 illustrate grid members for evaluating the human head in accordance with this invention.

An example of the use of the front view grid member 21 of FIG. 1 in determining head proportions is shown in FIGS. 3a, 3b and 3c. Grid member 21 is placed in front of a human head, or an image thereof, with the horizontal line 21b aligned with the bridge of the nose and vertical line 21a divides the head on a line passing through the V in the upper lip. Measurements are then made, such as by optical scanning of the grid or other suitable technique, to detect the points of intersection of the spaced horizontal lines on vertical grid line 21a with different portions of the front of the human head. This detection may indicate that the upper half of the head, as seen in FIG. 3a, is shorter than the lower half; or as shown in FIG. 3b, that the upper head half and the lower head half are equal in height; or as shown in FIG. 3c, that the upper head half is longer than the lower half.

Figure 7A:
FIGS. 7a and 7b illustrate the detection of differences between ear level and eye level.
Figure 7B:
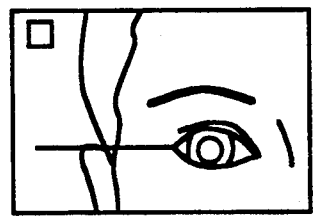

An example of the use of member 21 in determining the relationship between eye level and the top of the ear is shown in FIGS. 7a and 7b. Using horizontal line 21b aligned with the center of the eyes, measurements can be made to determine whether the top of the ear is even with the eye (FIG. 7b) or is above the eye level (FIG. 7a).

The grid 21 may also be utilized, as illustrated in FIGS. 4a and 4b, to detect the relative sizes of the right and left sides of the head. Grid 21 is again placed in front of the person's face or an image thereof with horizontal line 21b aligned with the bridge of the nose and vertical line 21 aligned through the V in the upper lip. Measurements are then made to detect the intersection of the graduated vertical lines on reference line 21a with different portions of the right and left sides of the head. Comparison of the detected values for each side provides an indication as to whether the right side of the face is larger (FIG. 4a), or the left side is larger (FIG. 4b). This information, either alone or in conjunction with other measurements, may be used in the selection of an appropriate hair style.

Figure 2:
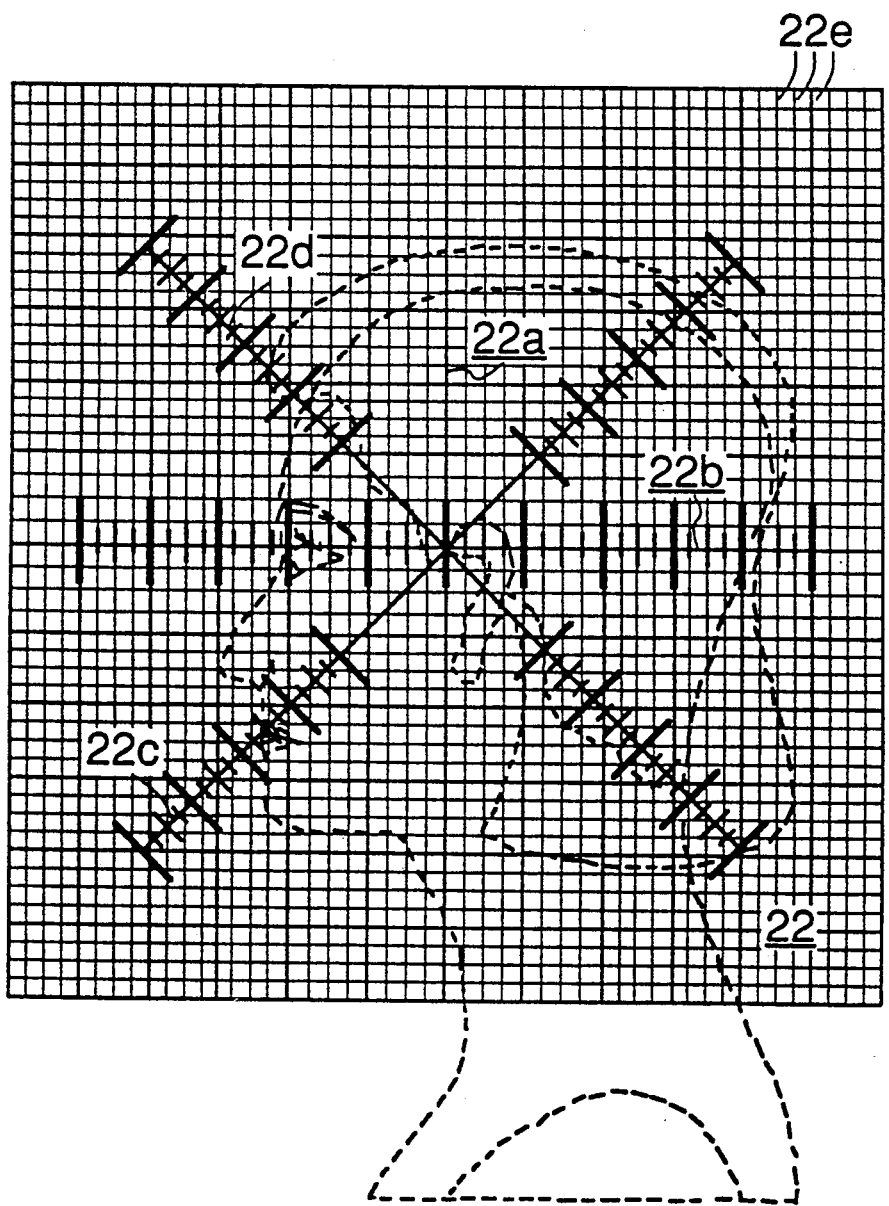

FIG. 2 illustrates a transparent member 22 having scaled graduations thereon which are useful in analyzing the human head from the side. Member 22 includes a vertical centerline 22a having graduated horizontal markings thereon. Member 22 also includes a graduated horizontal line 22b and two angled graduated lines 22c and 22d. The ideal head should be divided equally in front of the ear, as shown by centerline 22a in FIG. 2. Member 22 also preferably has an overlying grid pattern 22e thereon as described above for member 21.

Figure 5A:
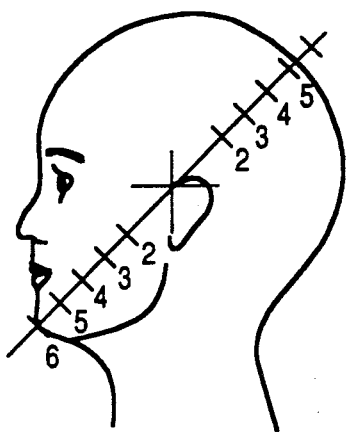
FIGS. 5a, 5b and 5c illustrate the invention applied to the detection of the chin-to-ear and ear-to-crown relationship.
Figure 5B:
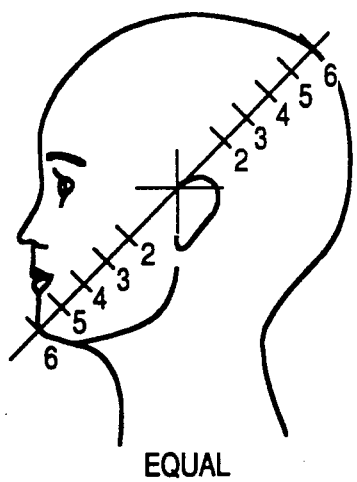
Figure 5C:
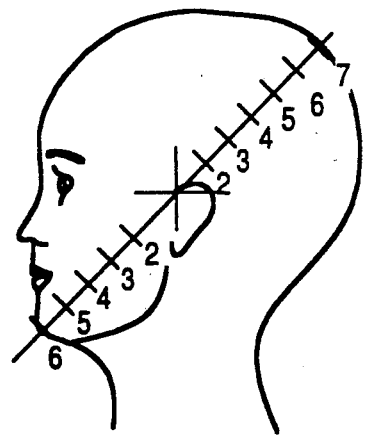

An example of the use of the member 22 in detecting the relationship of the chin-to-ear distance to the ear-to-crown distance is shown in FIGS. 5a, 5b and 5c. In this measurement, member 22 is aligned with the point of convergence of lines 22a, 22b, 22c and 22d located at the forward point of the upper ear. Measurements are then made on angled graduated line 22c of the distance from the chin to the front of the ear and the distance from the front of the ear to the crown of the head. Comparison of these detected measurements will indicate that the ear-to-crown distance is smaller than the chin-to-ear distance (FIG. 5a), that it is larger (FIG. 5c), or that these distances are equal FIG. 5b.

Figure 6A:
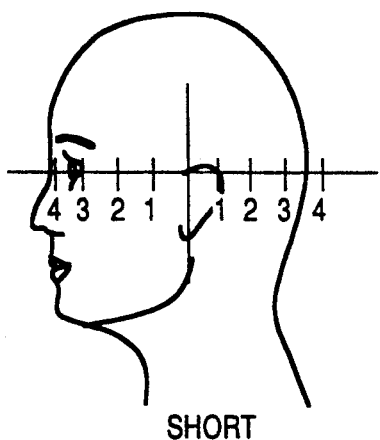
FIGS. 6a, 6b and 6c show the detection of differences in the nose bridge-to-ear distance and ear-to-the back of the head distance of a human head.
Figure 6C:
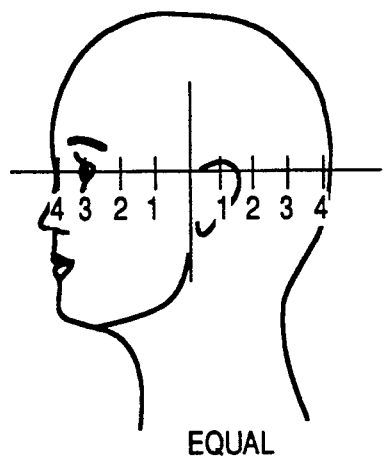
Figure 6B:
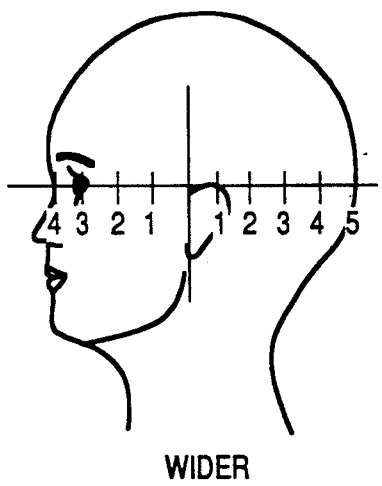

FIGS. 6a, 6b and 6c illustrate the use of member 22 to detect the relationship of the distance between the nose bridge and the front of the upper ear to the distance between the front of the ear to the back of the head. In this, measurements are made along horizontal graduated line 22b and the resulting measurements provide an indication that the bridge to ear distance is smaller (FIG. 6b), that it is larger (FIG. 6a) or that these distances are equal (FIG. 6c).

Member 22 may also be used to generate information as to whether the head is centered on the shoulders or whether it is positioned forward on the shoulders. If it is forward, this indicates, for example, that there needs to be volume in the back of a hair style to make the head appear as if it is more inclined back than it really is.

I claim:

1. A method for measuring characteristics of a human head comprising the steps of:

positioning a transparent grid member adjacent the front of a human head or an image of a human head;

said grid member including:

a vertical centerline aligned with the center of the bridge of the nose of the human head;

said vertical center line having a plurality of spaced horizontal scaling lines;

said grid member also having a horizontal centerline which crosses said vertical centerline;

said horizontal centerline having a plurality of spaced vertical scaling lines thereon;

measuring the distance from said horizontal centerline on said vertical centerline to the top of said head;

measuring the distance from said horizontal centerline on said vertical centerline to the bottom of said head; and comparing said measured distances to determine the relative proportions of the upper half of said head and the lower half of said head.

2. A method in accordance with claim 1 including the steps of:

measuring the distance from said vertical centerline on said horizontal centerline to the right edge of said head;

measuring the distance from said vertical centerline on said horizontal centerline to the left edge of said head; and comparing said measured distances to determined the relative proportions of the right half of said head and the left half of said head.

3. A method for measuring characteristics of a human head comprising the steps of:

positioning a transparent grid member adjacent the side of a human head or an image of a human head;

said grid member including;

a vertical centerline aligned with a line forward of the front of the ear of the human head;

said vertical centerline having a plurality of spaced horizontal scaling lines;

said grid member also having a horizontal centerline which crosses said vertical centerline;

said horizontal centerline having a plurality of spaced vertical scaling lines thereon;

measuring the distance on said horizontal centerline from a point forward of the ear of said head to the bridge of the nose of said head;

measuring the distance from said point forward of said ear to the back of said head; and comparing said measured distances to determine the relative proportions of said measured portions of said head.

4. A method for measuring characteristics of a human head comprising the steps of:

positioning a transparent grid member adjacent the side of a human head or an image of a human head;

said grid member including;

a vertical centerline aligned with a line forward of the front of the ear of the human head;

said vertical center line having a plurality of spaced horizontal scaling lines;

said grid member also having a horizontal centerline which crosses said vertical centerline;

said horizontal centerline having a plurality of spaced vertical scaling lines thereon;

said grid member having a pair of angled grid lines disposed at angles to said vertical centerline and said horizontal centerline;

measuring the distance on one of said angled grid lines from the chin of said head to the ear of said head;

measuring the distance on said one of said angled grid lines from the ear of said head to the crown of said head; and comparing said measured distances to determine the relative proportions of these distances.

* * * * *